US00PP36858P2

(12) United States Plant Patent
Hansoti

(10) Patent No.: US PP36,858 P2
(45) Date of Patent: Jul. 22, 2025

(54) ***SANSEVIERIA* PLANT NAMED 'Hansoti55'**

(50) Latin Name: *Sansevieria trifasciata*
Varietal Denomination: Hansoti55

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,642

(22) Filed: Dec. 23, 2024

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./373, 382
See application file for complete search history.

(56) References Cited

U.S. PATENT DOCUMENTS

PP30,342 P2 * 4/2019 Hansoti ..... A01H 5/12 Plt./382
PP36,357 P2 * 12/2024 Hansoti ..... Plt./382

* cited by examiner

*Primary Examiner* — Karen M Redden

(57) ABSTRACT

A new and distinct cultivar of *Sansevieria* plant named 'HANSOTI55' is disclosed, characterized by a dark grey-green marginal band 2 to 17 mm wide but occasionally up to 25 mm wide on both edges of the leaf. These dark bands along the edge give attractive definition to the leaf and the added green makes for a stronger plant. The dark foliage also has bright cream variegation with a broad central lighter grey-green band along the length of the leaf overlaid or veiled by a creamy overlayer, giving excellent colour to the plant Leaves of mature plants are less erect compared to the parent and even more reclined when compared to most other *Sansevieria* in the "Compact *Sansevieria* Group". The new cultivar can be classified in the Compact *Sansevieria* Group. The new variety is a *Sansevieria*, typically produced as an ornamental plant.

11 Drawing Sheets

Latin name of the genus and species: *Sansevieria trifasciata*.

Variety denomination: 'HANSOTI55'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI55'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI55' was discovered and selected by the inventor, Ashish Hansoti, as a single aberrant side shoot in early to mid-2018, within a planting of *Sansevieria trifasciata* 'Hansoti20' (U.S. Plant Pat. No. 30,342) mother plants grown at a nursery in Village Vangani, District Thane, Maharashtra State in Western India.

The side shoot, or pup, was isolated and subsequent offsets from this were harvested to give a number of plants, which were subjected to strict selection for appropriate characteristics that distinguish 'Hansoti55' from 'Hansoti20', most particularly a well-defined, dark green broad border on both edges of the leaves.

Asexual reproduction of the new *Sansevieria* cultivar by vegetative cuttings was first performed in April or May 2020 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI55', which in combination distinguish this *Sansevieria* as a new and distinct cultivar:

1. A dark grey-green marginal band, 2 to 17 mm wide but occasionally up to 25 mm wide on both edges of the leaf is the primary distinguishing characteristic of this invention from its parent 'Hansoti20'. These dark bands along the edge give great definition to the leaf and the added green makes for a stronger plant.
2. Bright cream variegated foliage with a broad central lighter grey-green band along the length of the leaf overlaid or veiled by a creamy overlayer, giving excellent colour to the plant.
3. Leaves of mature plants are less erect compared to the parent and even more reclined when compared to most other *Sansevieria* in the "Compact *Sansevieria* Group".

The new variety 'Hansoti55' is considered a variety of *Sansevieria* in the group denominated as the "Compact *Sansevieria* Group". The new variety presents an average of 7 to 9 leaves per plant when it reaches its saleable size (between 3-4 months from rooted liner). The new variety has a semi-erect growth habit and the entire plant can reach a height ranging between 20 and 25 cm. The leaves are of medium width (6 to 8 cm) measured at the widest part of the mature leaf under good growing conditions) and broad-lanceolate with a firm, waxy texture. The blades are thick or fleshy and slightly wavy. This variety also has an inverted triangle shape like most *Sansevieria* of the "Compact Group".

The new variety is moderately drought tolerant and adapts well to conditions of bright light and semi-shade (exterior and interior).

Overall, the new variety shows a bright variegated appearance with each leaf having three distinct longitudinal bands—the two dark green marginal bands of 2 to 17 mm and occasionally up to 25 mm wide; a broad central light green band veiled to varying degrees by a overlying layer of grey-cream tissue and a bright buttery yellow area between these two.

Superimposed on the whole leaf is the typical *Sansevieria trifasciata* cross banding—this is very prominent on the dark edge bands but also visible on the central broad band and very indistinct but still visible on careful inspection on the base bright yellow areas between the edge and central band.

Each leaf has a marginal band along each edge of the leaf that is darker grey green, varying in width from just 2 mm to 17 mm and may be as wide as 25 mm. These marginal bands have prominent horizontal cross banding of light and dark grey-green, as is common in most *Sansevieria trifasciata* cultivars. The two colours in this cross-banding are near RHS Greyed-Green 191A (Lighter grey-green) and Greyed-Green N189A (Darker Grey-green).

Between these two distinct border bands is a broad central band. This zone consists of varying widths of lighter grey-green streaks and bands. This central area of the leaf can consist of just a few strands of green to a wide band of various shades of grey green, all covered with a thin layer of creamy tissue. The depth of this overlying tissue determines the colour of these central bands-from a dark green near RHS Greyed-Green N189A to a lighter green similar to Yellow-Green N144D or even a very light Greyed-Green 191C.

The area between the dark grey-green marginal bands and the central band is plain buttery-yellow. The butter yellow area varies from a relatively narrow zone 10-15 mm wide on either side of the central bands to an almost complete area between the dark border bands. The colour of this bright yellow zone is near RHS Yellow 2B or 3C. Occasionally this creamy yellow zone is invaded by streaks of darker green similar to the border bands.

What is important to the overall look of each leaf and the whole plant is the strong contrast between the dark green border bands and this creamy yellow central zone—the plants look very highly variegated and richly coloured compared to other *Sansevierias* in the "Compact *Sansevieria* Group".

Backside of the leaves is essentially the same colouring and pattern as the front with prominent dark grey-green marginal bands but somewhat narrower—typically 2 to 10 mm wide. The central green band is also much subdued and the overall look is a creamy yellow central zone between the marginal green bands. On the back side of the leaf the typical *Sansevieria trifasciata* cross hatching is more visible, very prominent on the edge green bands but obvious even on the creamy areas.

PARENTAL COMPARISON

Plants of the new *Sansevieria* 'HANSOTI55' are similar to plants of the parental cultivar, however, 'HANSOTI55' differs in the characteristics described in Table 1.

TABLE 1

Comparison of Parental variety 'Hansoti20' (U.S. Plant Pat. No. 30,342) with new variety 'Hansoti55'

| | Characteristic | Parent *S. trifasciata* 'Hansoti20' | New cv 'Hansoti55' |
|---|---|---|---|
| 1. | Overall Colour | Bright, overall creamy yellow look with central broad band of light green and streaks and bands of variable width and bright green colour along edges. | Less creamy overall look because the prominent dark grey-green bands along leaf edges that encroach into the creamy yellow areas. But higher level of contrast giving a rosette that looks highly variegated. |
| 2. | Border | Very variable, ill-defined, light, stippled, often discontinuous band of bright green to grey green - typically around 10 mm wide but may be entirely absent or up to 25 mm wide. Usually broad and prominent on one side of leaf and minimal or absent on the opposite side. | Dark grey-green, prominent border, 2 to 17 mm or more wide, along both sides of leaf. The typical horizontal striations of *S. trifasciata* are very prominent here on these marginal bands. |
| 3. | Leaf Centre | Broad, green band lightly veiled with creamy tissue and surrounded by broad area of bright cream. | Central diffuse green band is broader, lighter, overlaid with more creamy tissue. Surrounding cream zone is narrower, being covered to large extent by the dark green marginal band. |

In brief, the new 'Hansoti55' is basically similar to the parent cultivar 'Hansoti20' but with additional broad prominent dark grey-green borders along both leaf sides, giving better definition to the leaf and a stronger plant.

The variety 'Hansoti20' gave rise to the variety 'Hansoti55'. 'Hansoti20' shows somewhat less vigour than 'Hansoti55', typically has fewer leaves per plant (6-7) most likely due to the paucity of chlorophyll in this parent cultivar compared to the new cultivar 'Hansoti55'.

The parent 'Hansoti20' presents as an overall cream coloured plant. On the side of each leaf there are bands of green colour, highly variable in width (from almost absent to 25 mm or even more wide) and in colour (ranging from a light pastel green to light grey-green). Typically, this edge band is only present on one edge of each leaf.

In comparison, 'Hansoti55' presents as a somewhat less creamy plant: the central green band with creamy overlay is wider and the marginal bands (2 to 15 mm wide)-prominent dark, grey-green-also encroach on the creamy yellow area.

These two together restrict the creamy yellow area compared to the same in 'Hansoti20'. Each leaf has the thin 1-2 mm very dark green edge and then inside that the prominent dark grey-green band into which lines of cream sometimes enter, giving the leaf a "feathered" or "Painted" look.

This overall difference in the amount of green in the leaf gives a distinctly different look from the parent while also increasing the cultivars growth speed and its overall vigour.

COMMERCIAL COMPARATOR

Plants of the new *Sansevieria* 'HANSOTI55' are similar to the commercial variety *Sansevieria trifasciata* 'Futura Superba', unpatented. Plants of the new *Sansevieria* 'HANSOTI55' differ from plants of the commercial cultivar in the characteristics described in Table 2.

TABLE 2

Comparison between well-known variety 'Futura Superba' and the new variety 'Hansoti55'

| | Characteristic | Comparable Cultivar *S. trifasciata* 'Futura Superba' | New cv 'Hansoti55' |
|---|---|---|---|
| 1. | Leaf size | Up to 40 cm or even longer | 25 to 30 cm long |
| 2. | Number of leaves | 4 to 6 leaves - fewer leaves | 7 to 9 leaves - more leaves |
| 3. | Variegation Pattern | Overall Dark Green leaves with prominent transverse markings and a creamy yellow border band. | Overall Creamy leaves with dark grey-green border bands and a broad central grey-green band with creamy yellow colour in between. |
| 4. | Border variegation | 2 to 15 mm wide creamy yellow band with subdued transverse banding. | 2 to 17 mm or wider dark grey-green band with prominent transverse banding. |
| 5. | Central Variegation | None - Grey-Green leaf with no central variegation, but with prominent transverse banding so typical of *S. trifasciata* in leaf central area. | Creamy yellow with prominent grey-green broad band in centre covered by layer of creamy tissue and with cream variegation on either side of this central band. Subdued transverse banding visible. |

BRIEF DESCRIPTION OF THE PHOTOGRAPHS

The accompanying photographs illustrate the overall appearance of the new *Sansevieria* cultivar 'HANSOTI55' showing the colors as true as is reasonably possible with colored reproductions of this type. Colors in the photographs may differ slightly from the color value cited in the detailed botanical description which accurately describe the color of 'HANSOTI55'.

These pictures illustrate the plant form which is the unique characteristic of 'HANSOTI55' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

FIG. 1, FIG. 2 and FIG. 3: Show a plant of *Sansevieria* 'Hansoti55' in a 12 cm diameter pot from various angles. The photos illustrate top as well as bottom of leaves and the leaf arrangement.

FIG. 4, FIG. 5 and FIG. 6: Show different views of a tray of 'Hansoti55' with 8 plants in 12 cm pots, showing uniformity across multiple plants.

FIG. 7 shows the three cultivars cited in this patent application pictured together for easy comparison. The new cultivar 'Hansoti55' (Top) showing an overall cream coloration but with dark grey green edge bands. The non-patented parent cultivar-'Ghost' (Bottom Left) showing creamier overall colour and indistinct bright green border coloration. The old, standard cultivar 'Futura Superba' (Bottom Right) representing the classic "Compact *Sansevieria* Group" showing bigger, broader, more robust leaves and fewer leaves. The variegation pattern of the three cultivars differs.

Figure 1:
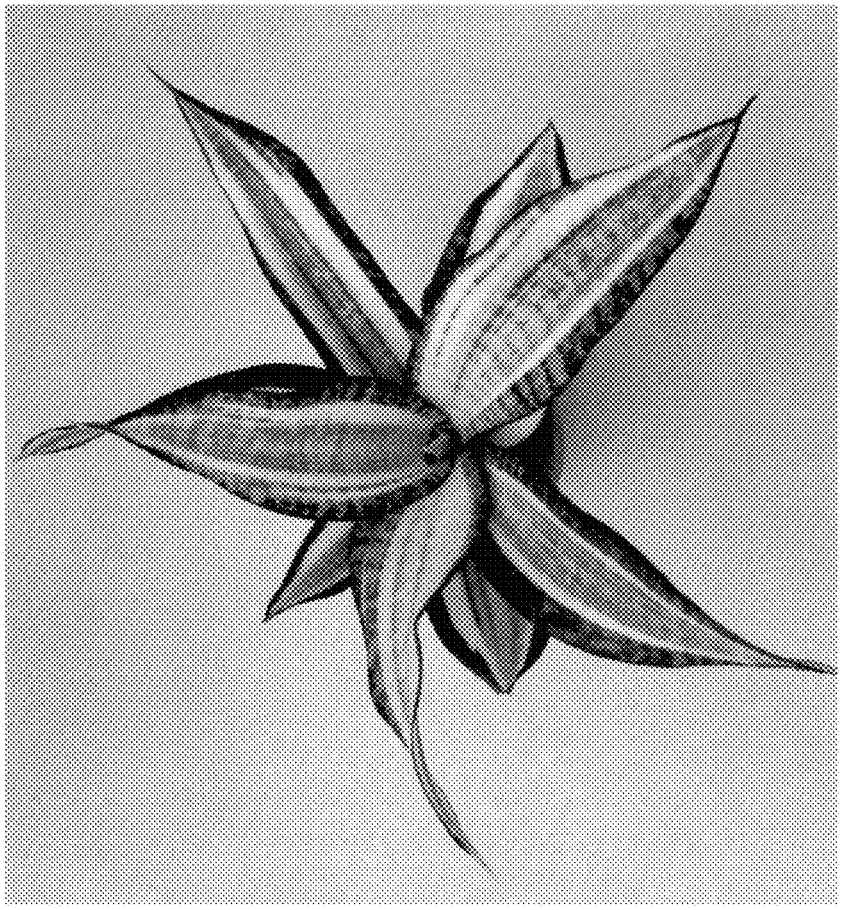
Figure 2:
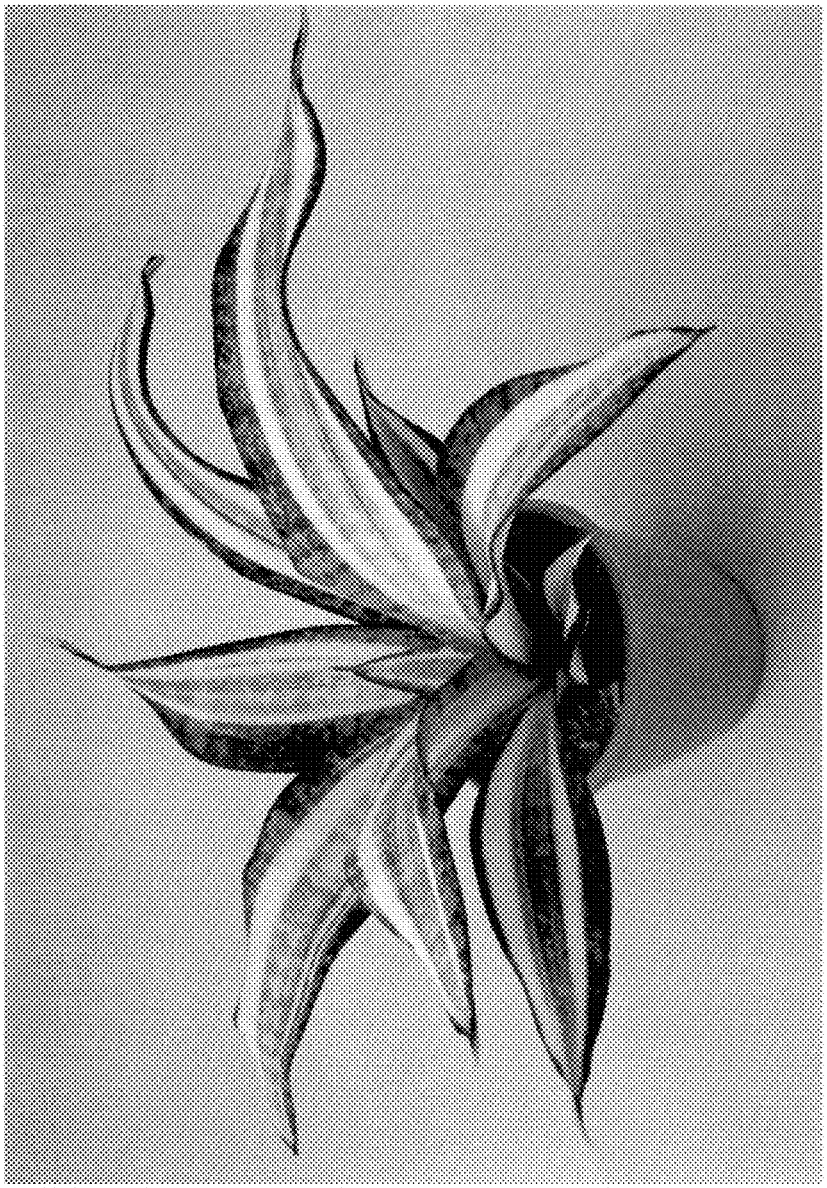
Figure 3:
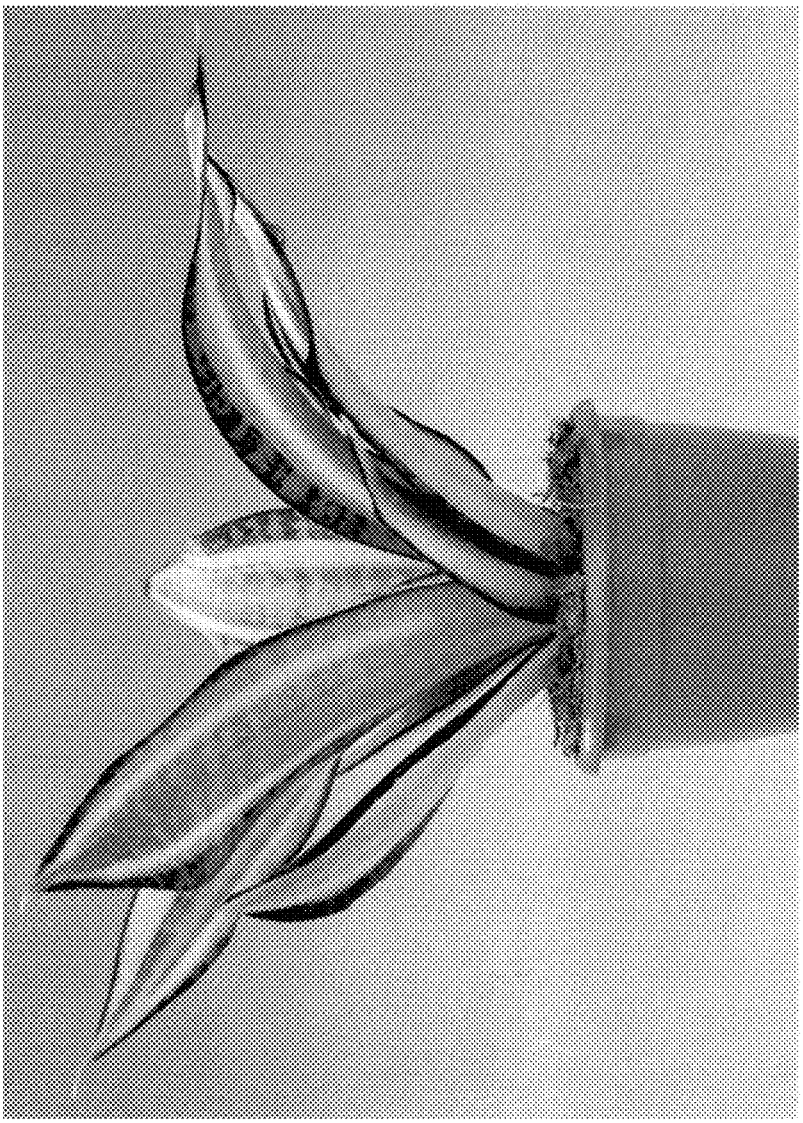
Figure 4:
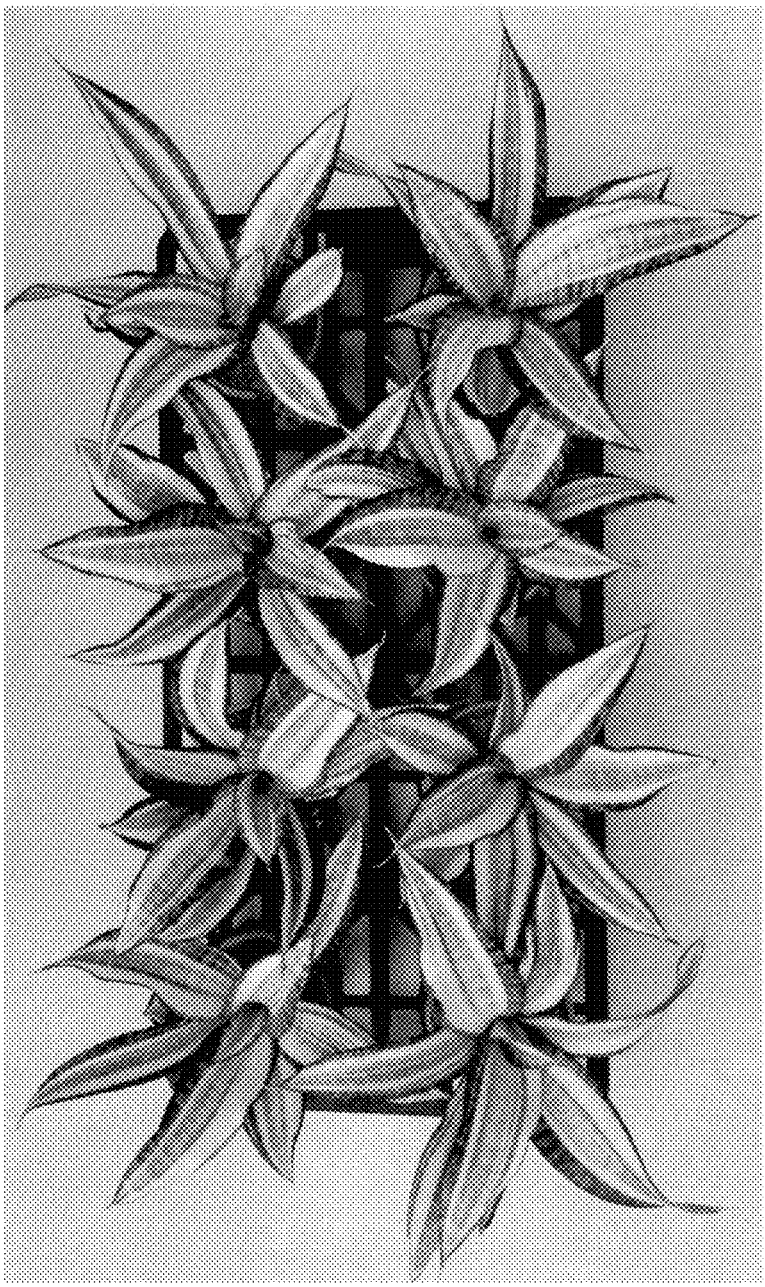
Figure 5:
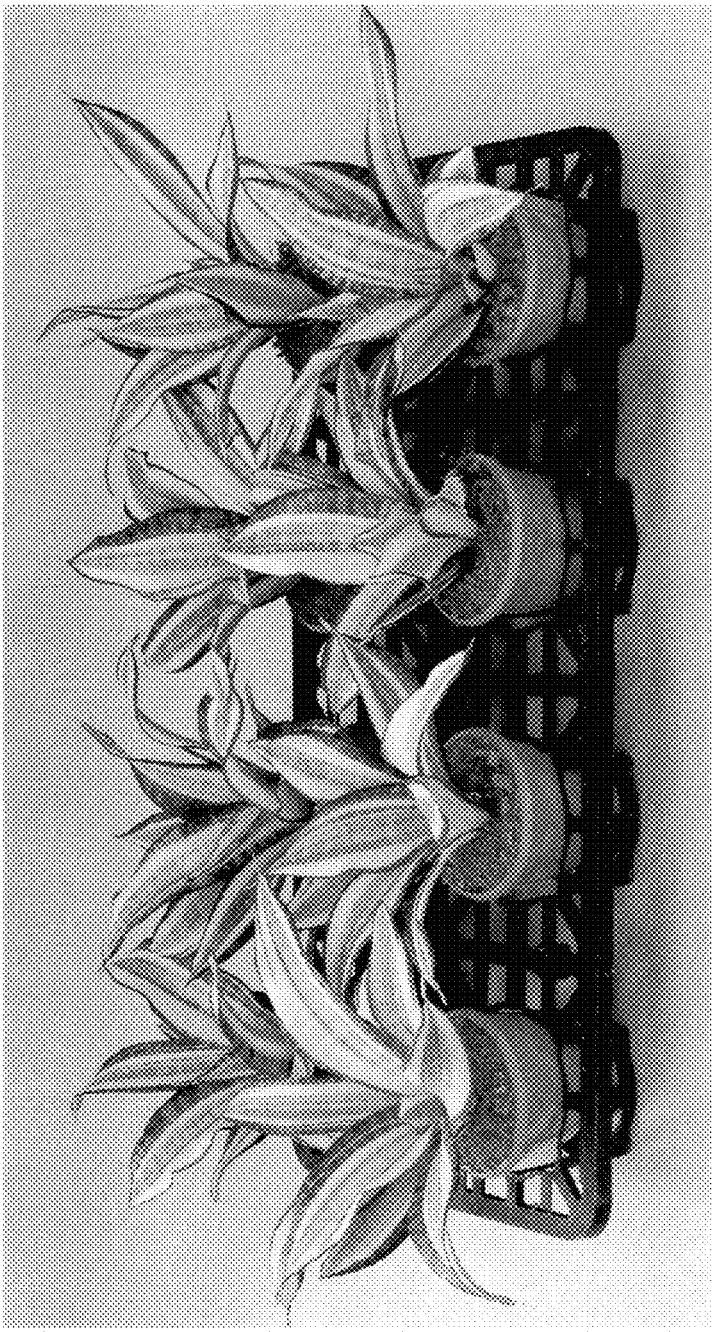
Figure 6:
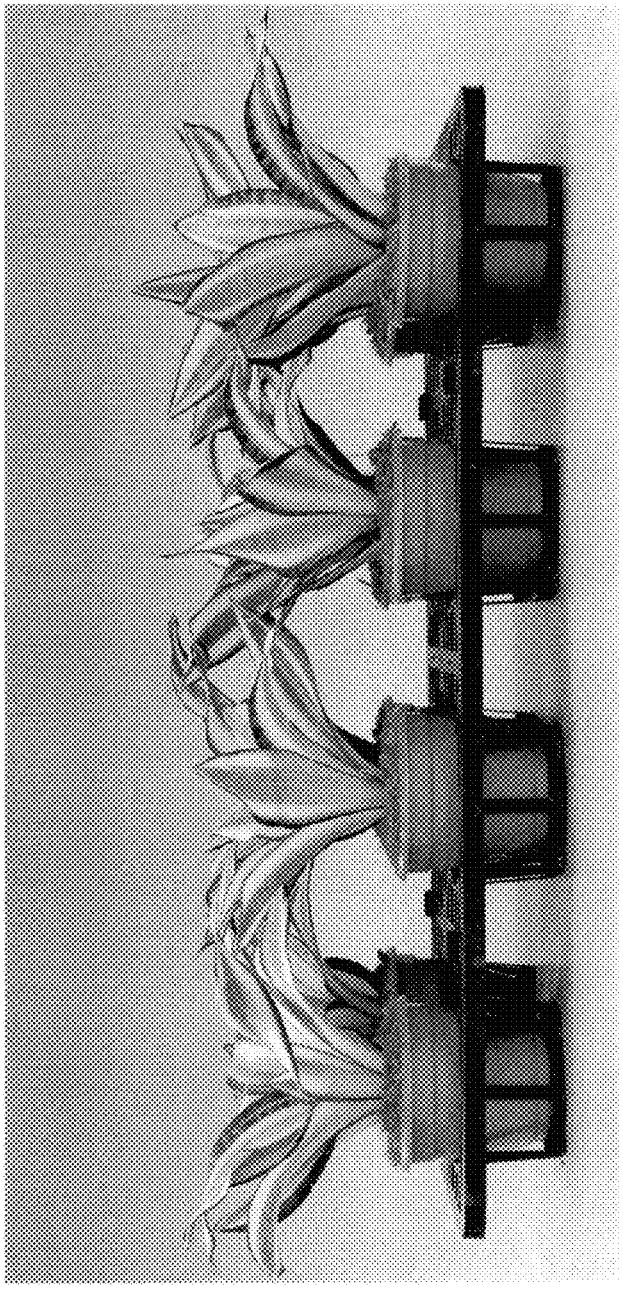
Figure 7:
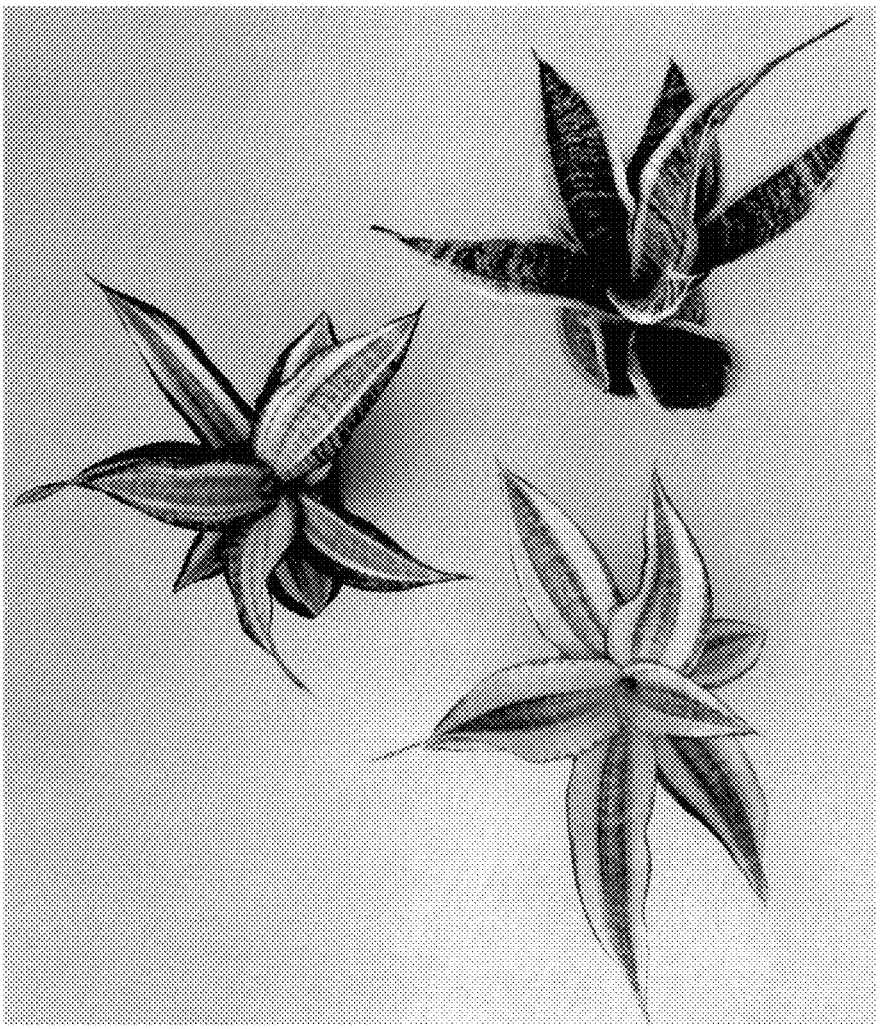
Figure 8:
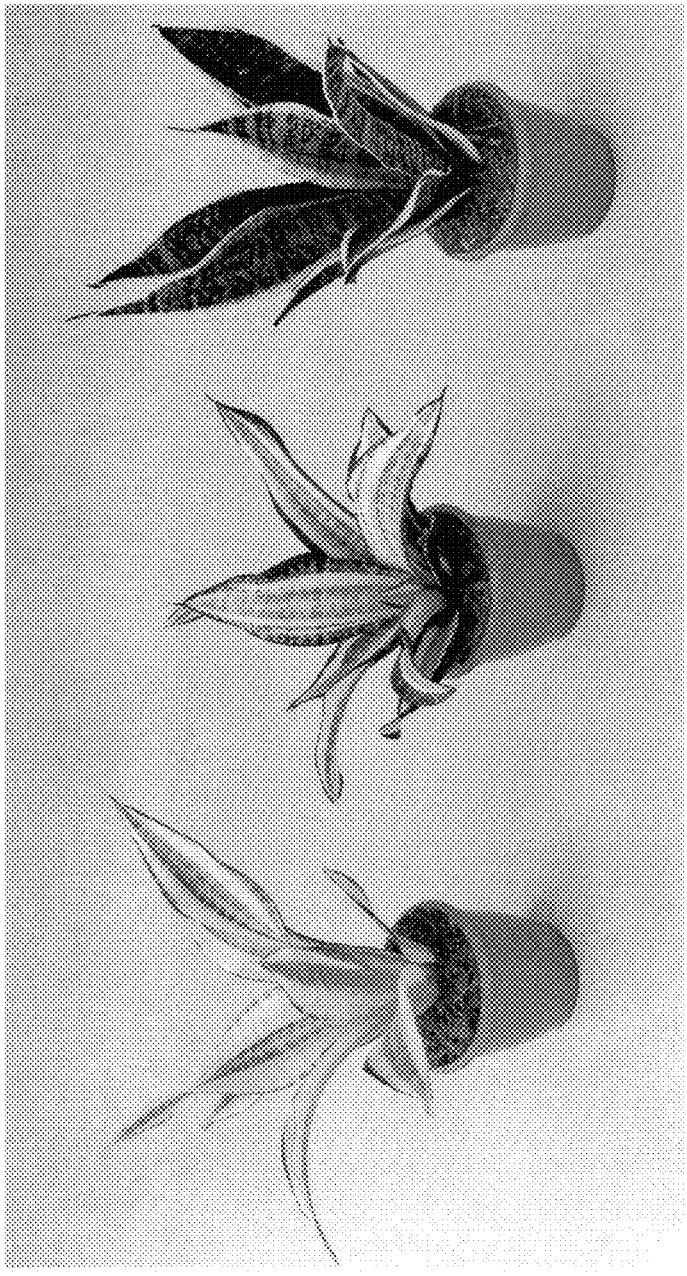
FIG. 8 shows the three cultivars cited in this patent application pictured in an angular view. 'Futura Superba' is on the left, 'Hansoti55' center and 'Ghost' right.
Figure 9:
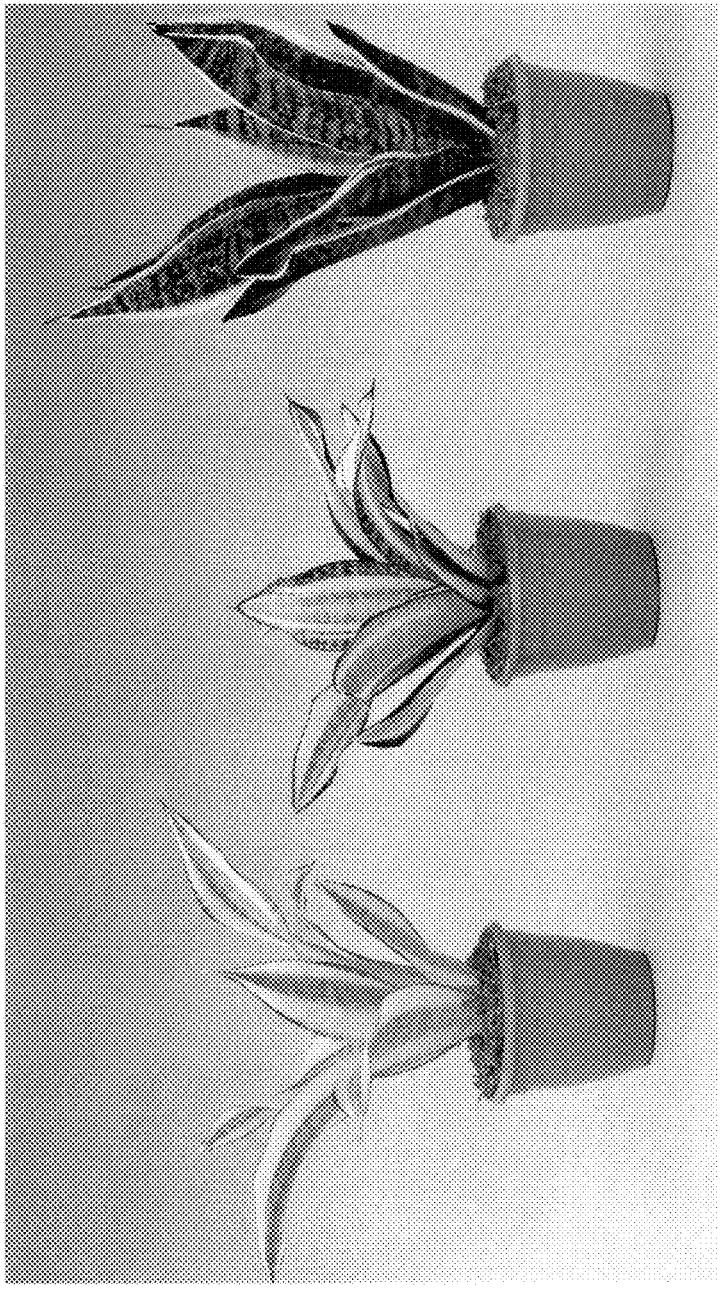
FIG. 9 shows the three cultivars cited in this patent application pictured in a side view. 'Futura Superba' is on the left, 'Hansoti55' center and 'Ghost' right.
Figure 10:
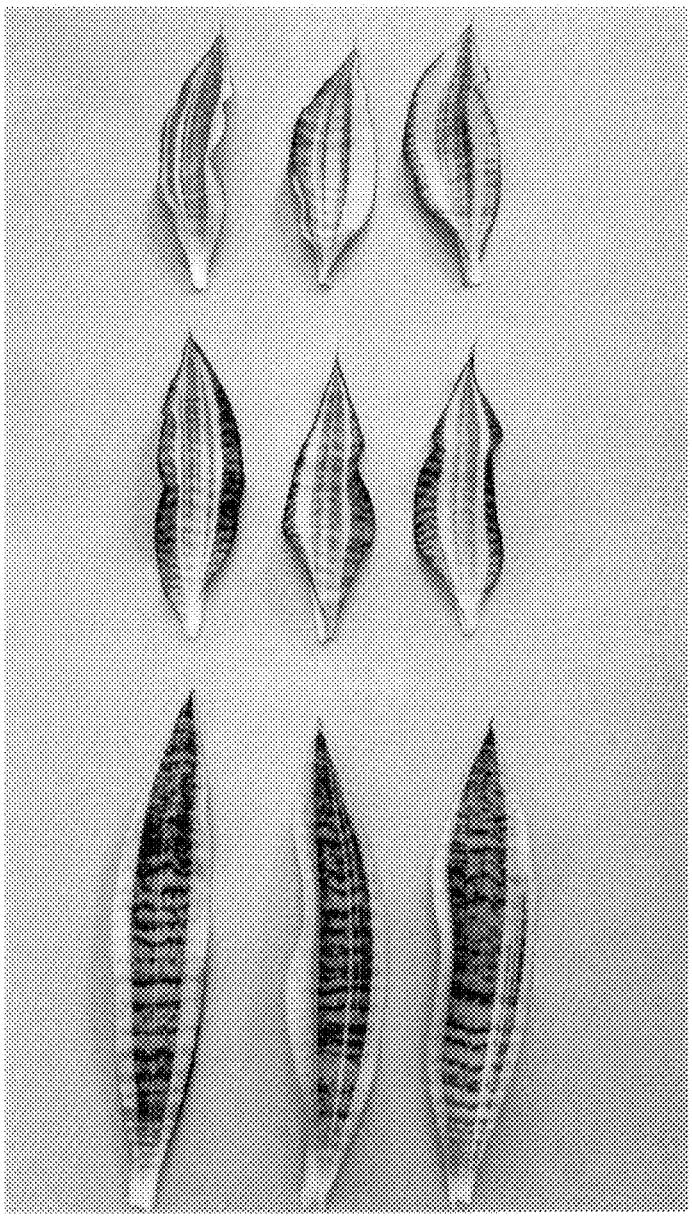
FIG. 10 shows individual leaves adaxial (top) surface of *Sansevieria* 'Hansoti55' (Center), the parental variety 'Hansoti20' (Top row)-and leaves of *Sansevieria* 'Futura Superba' (Bottom Row) compared to show the differences in variegation pattern and color.
Figure 11:
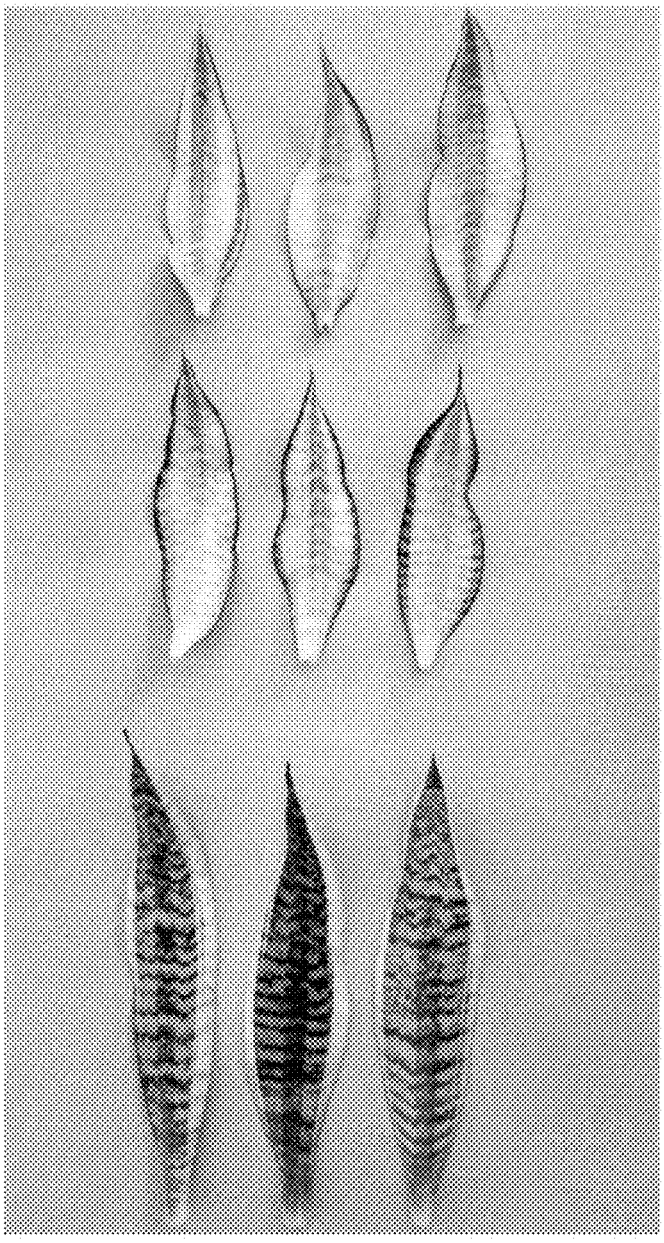

FIG. 11: shows individual leaves abaxial (bottom) surface of *Sansevieria* 'Hansoti55' (Center), the parental variety 'Hansoti20' (Top row)—and leaves of *Sansevieria* 'Futura Superba' (Bottom Row) compared to show the differences in variegation pattern and color.

DETAILED BOTANICAL DESCRIPTION

The new *Sansevieria* 'HANSOTI55' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI55' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertiliser of 13:11:11 Type 360-days release at 1 kilo/cubic meter of media, liquid feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used. It should be noted that colors in *Sansevieria* are somewhat variable depending on light levels, nutrition balance, age of plant and other factors. The variety 'HANSOTI55' has, apart from the unusual overall silvery-green look, two major distinctive features compared to its parent plant-there is no light golden yellow border band running along the edge of the and the typical transverse banding of *Sansevieria trifasciata* is much less prominent.

The photographs and descriptions were taken during the monsoon season in Asle, District Satara, Maharashtra State, India when outdoor day and night temperatures were 25° C. to 30° C. The age of the plants described is 3-4 months from rooted liners.

Botanical classification: *Sansevieria trifasciata* 'HANSOTI55'.

General information:

*Parentage.*—*Sansevieria trifasciata* 'Hansoti20', U.S. Plant Pat. No. 30,342.

*Optimal growth conditions.*—

*Light intensities.*—High adaptability to outdoor or indoor conditions but needs some shade in hot climates. Shade levels of 35% to 75% depending on season to give maximum light intensity of 350 to 500 $\mu mol/m^2/s$.

*Temperature.*—Day: 25° C. to 35° C. Night: 15° C. to 25° C.

*Temperature tolerance.*—Tolerant to a low temperature of about 6° C. and a high temperature of 39° C. and above — very heat tolerant.

*Fertilization.*—Constant feed of 100 ppm N, 20 ppm P and 100 ppm K is used along with micronutrients with occasional leaching. Media incorporation of slow release 13:11:11 Type 360 days release at 1 kg/cubic meter of media.

*Growth regulators.*—Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—25 to 30 days at 25° C. to 30° C.

*Time to produce a rooted liner.*—About 45 days at 25° C. to 30° C.

*Time to produce ready* 12 *cm potted plant from liner.*—About 12 to 15 weeks at 25° C. to 30° C.

Plant:

*General appearance and form.*—Monocot; leaf bases arranged in a rosette around growth point.

*Height.*—About 20 to 25 cm when grown in 12 cm pots.

*Spread.*—About 30 to 35 cm when grown when grown in a 12 cm size container.

*Growth rate and habit.*—Moderate; semi-upright.

*Shape.*—Inverted triangle.

*Fragrance.*—None.

*Stem.*—Modified (rhizomes with erect foliage).

*Rosette height.*—About 14 to 16 cm height from top of pot when grown in 12 cm size container.

*Rosette diameter.*—About 18 to 22 cm.

*Texture.*—Smooth, waxy.

*Strength.*—Strong and durable.

*Internode length.*—About 1 to 2 mm.

Foliage:

*Quantity.*—About 7 to 9.

*Arrangement and attachment.*—Single, alternate; leaf bases arranged stiffly in a rosette around central growth point.

*Leaf length.*—About 20 to 30 cm.

*Leaf width.*—About 6 to 8 cm, occasionally more.

*Overall shape of leaf.*—Lanceolate.

*Apex shape.*—Acute, triangular and aristate, with soft tip.

*Base shape.*—Plane.

*Margin.*—Sharp, smooth.

*Texture.*—Upper Surface: Smooth and waxy texture.

*Texture.*—Under Surface: Smooth and waxy texture.

*Pubescence.*—None.

*Color of mature leaf.*—The depth of the creamy tissue overlying the deeper green tissue determines the colour of the central bands-from a dark green near RHS Greyed-Green N189A to a lighter similar to Yellow-Green N144D or even a very light 191C. The colour of the bright yellow zone on either side of central green band is near Yellow 2B or 3C.

*Margins.*—The transverse banding gives two colours in this band and they are near RHS Greyed-Green 191A (Lighter grey-green) and Greyed-Green N189A (Darker Grey-green).

*Venation pattern.*—Longitudinal/parallel leaf shape.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs (*Rhizoecus pritchardi*). Typical pests include *Pseudococcidae longispinus* and *Tetranychus urticae.*

*Disease resistance.*—Occasionally shows *Anthracnose* and leaf spots but largely disease-free from clean mother stock and appropriate disease mitigation measures undertaken.

*Fruit/seed production.*—No fruits/seeds detected to date.

What is claimed is:

1. A new and distinct cultivar of *Sansevieria* plant named 'HANSOTI55' as herein illustrated and described.

* * * * *